United States Patent [19]
Cope

[11] Patent Number: 6,110,183
[45] Date of Patent: Aug. 29, 2000

[54] SUTURE ANCHOR DEVICE

[75] Inventor: Constantin Cope, Elkins Park, Pa.

[73] Assignee: Cook Incorporated, Bloomington, Ind.

[21] Appl. No.: 09/219,330

[22] Filed: Dec. 22, 1998

[51] Int. Cl.$^7$ .................................................. A61B 17/00
[52] U.S. Cl. ........................................................ 606/139
[58] Field of Search .......................... 606/139, 144–148, 606/232; 112/169, 80.03; 604/104, 168

[56] References Cited

U.S. PATENT DOCUMENTS

| | | | |
|---|---|---|---|
| Re. 34,021 | 8/1992 | Mueller et al. | 604/51 |
| 3,521,640 | 7/1970 | Carey et al. | |
| 4,006,747 | 2/1977 | Kronenthal et al. | |
| 4,077,412 | 3/1978 | Moosun | |
| 4,235,238 | 11/1980 | Ogiu et al. | |
| 4,669,473 | 6/1987 | Richards et al. | |
| 5,071,405 | 12/1991 | Piontek et al. | 604/96 |
| 5,085,661 | 2/1992 | Moss | 606/139 |
| 5,123,914 | 6/1992 | Cope | 606/232 |
| 5,207,679 | 5/1993 | Li | 606/72 |
| 5,213,575 | 5/1993 | Scotti | 604/95 |
| 5,429,598 | 7/1995 | Waxman et al. | 604/51 |
| 5,470,337 | 11/1995 | Moss | 606/139 |
| 5,531,678 | 7/1996 | Tomba et al. | 604/51 |
| 5,613,974 | 3/1997 | Andreas et al. | 606/144 |
| 5,626,614 | 5/1997 | Hart | 606/232 |
| 5,797,929 | 8/1998 | Andreas et al. | 606/148 |

OTHER PUBLICATIONS

Cope, "Suture Anchor for Visceral Drainage" *Am J Roentgenol*, vol. 146, pp. 160–162 (1986).

"Percutaneous Articulated T–Tube" in *Diagnostic and Interventional Products for Radiology—Cook Incorporated Catalog Supplement*, Fall 1994, p. 44.

Brown et al., "Controlled Percutaneous Gastrostomy: Nylon T–Fastener for Fixation of the Anterior Gastric Wall" *Radiology*, vol. 158, No. 2, 1986, pp.543–545 (1986).

Coleman et al., "Percutaneous Enterostomy with the Cope Suture Anchor" *Radiology*, vol. 174, pp. 889–891 (1990).

Shatz et al., "Laparascopic Suturing Technique for Enteral Access Procedures" *Surgical Endoscopy* vol. 8, No. 6, pp. 717–718 (1994).

*Primary Examiner*—Michael Buiz
*Assistant Examiner*—Vikki Hoa B. Trinh
*Attorney, Agent, or Firm*—Woodard, Emhardt, Naughton Moriarty & McNett

[57] ABSTRACT

A suture anchor device, a visceral anchor for anchoring a viscus to a body wall, a kit for anchoring a viscus to a body wall and a method for anchoring a viscus to a body wall are described. The method and device reduce the probability of injuring the interior of a viscus as a large gauge needle is not required to deliver the visceral anchor. In one embodiment, the distal end of the visceral anchor may function as a dilator.

54 Claims, 12 Drawing Sheets

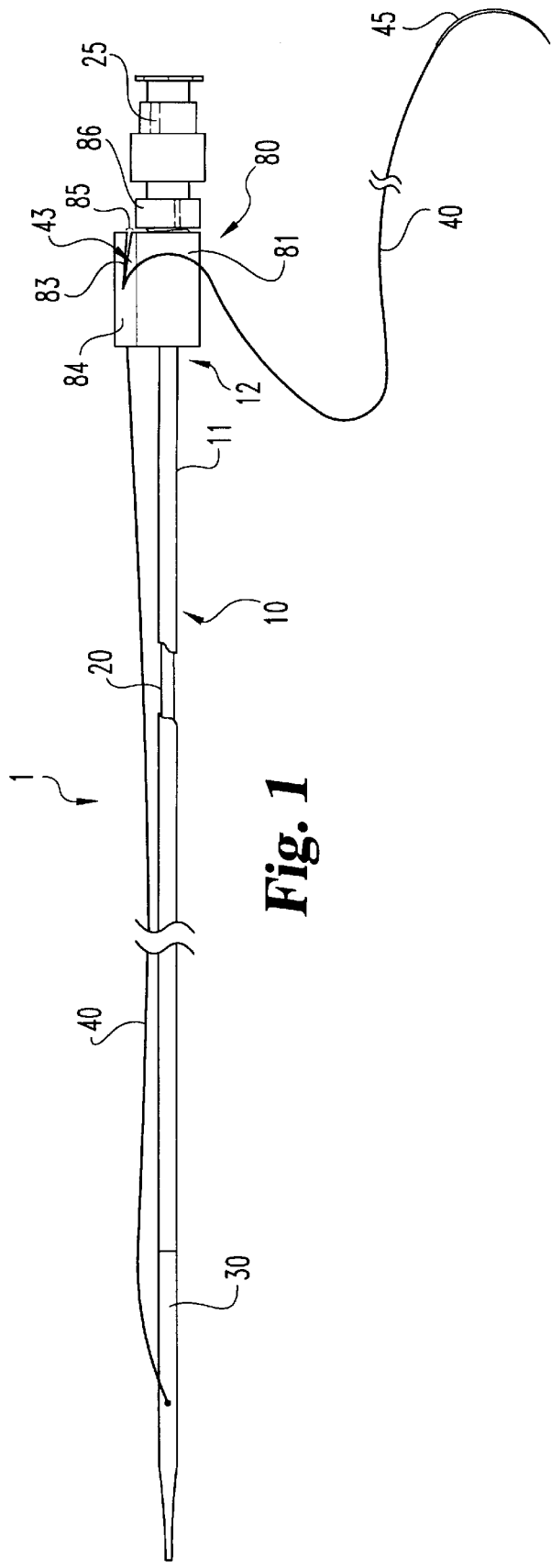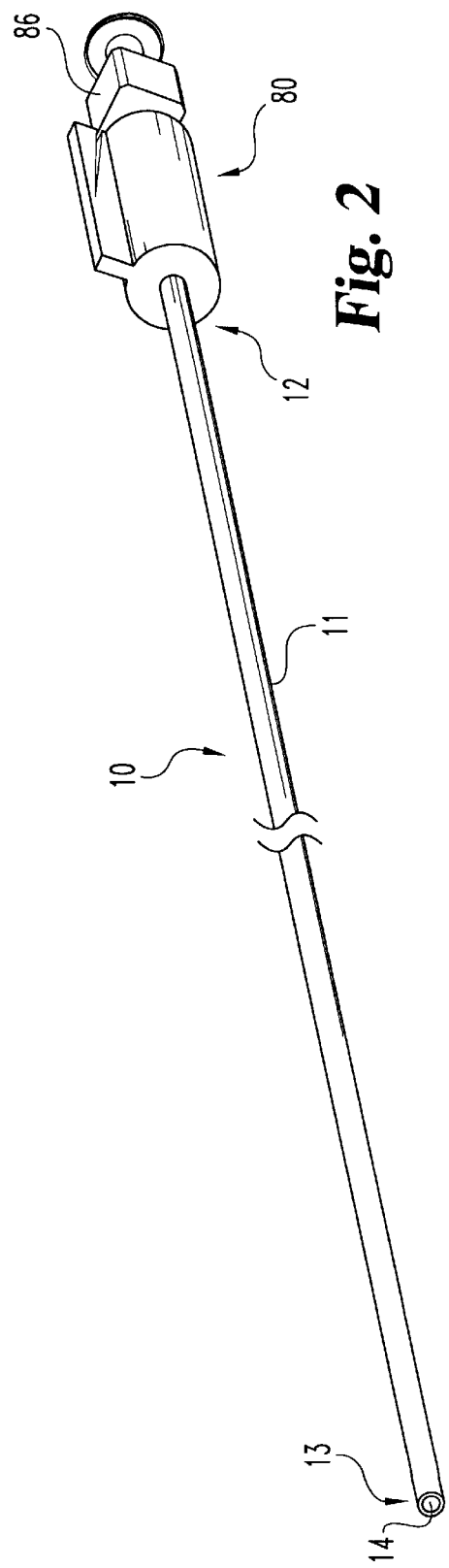

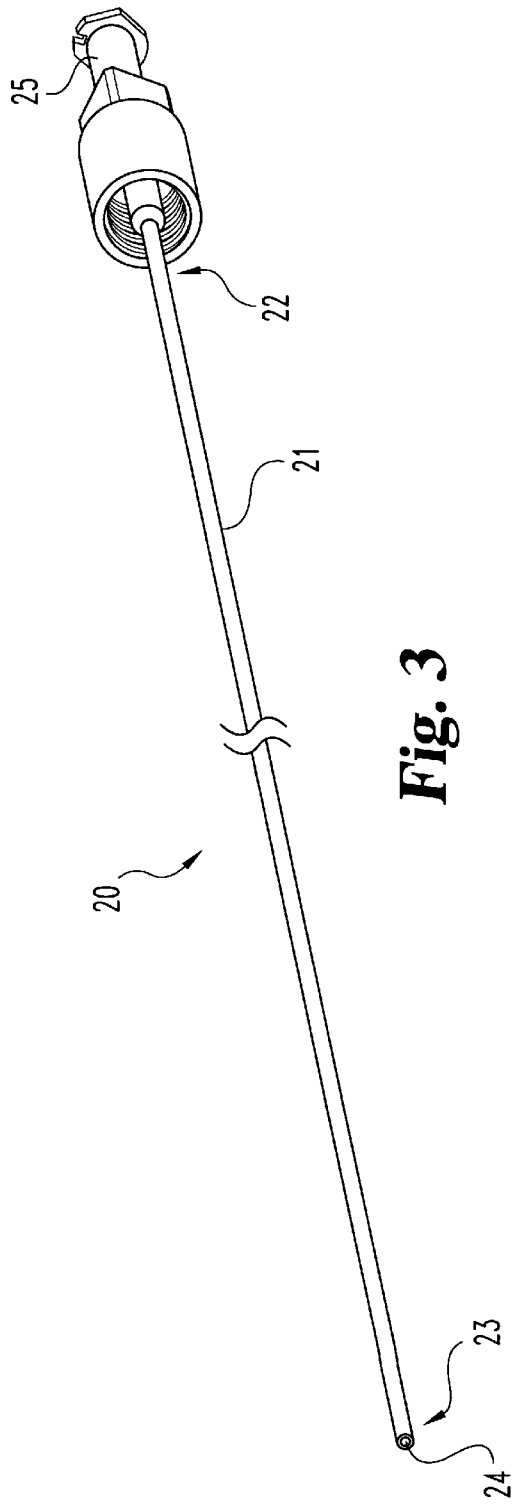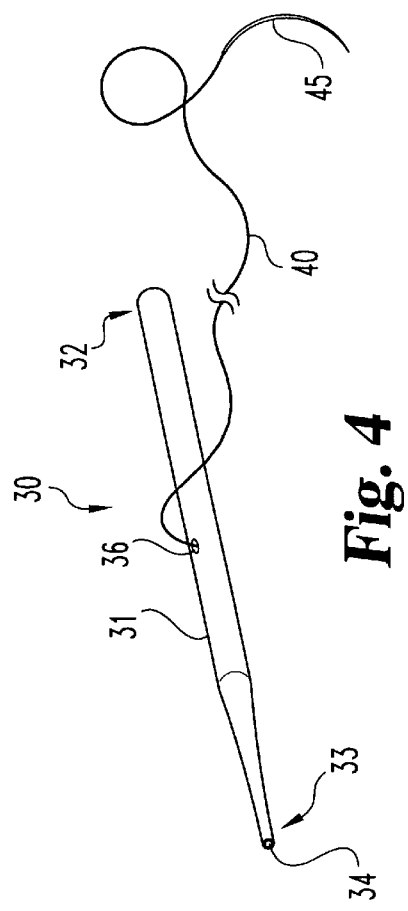

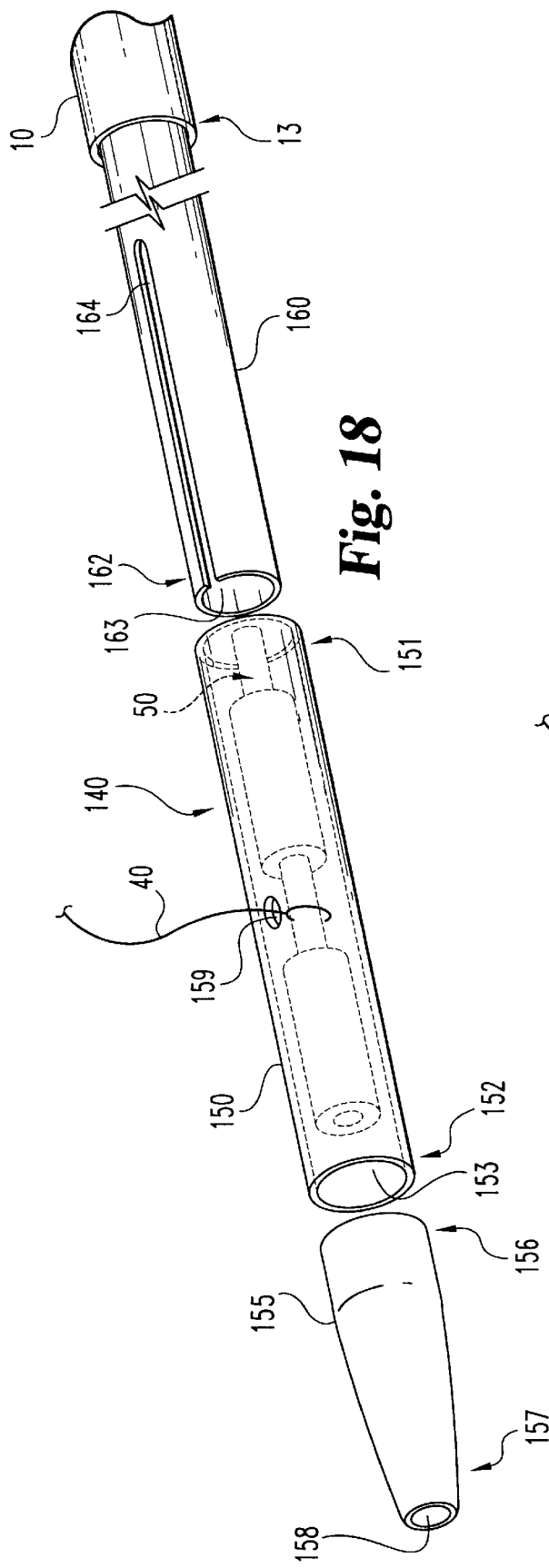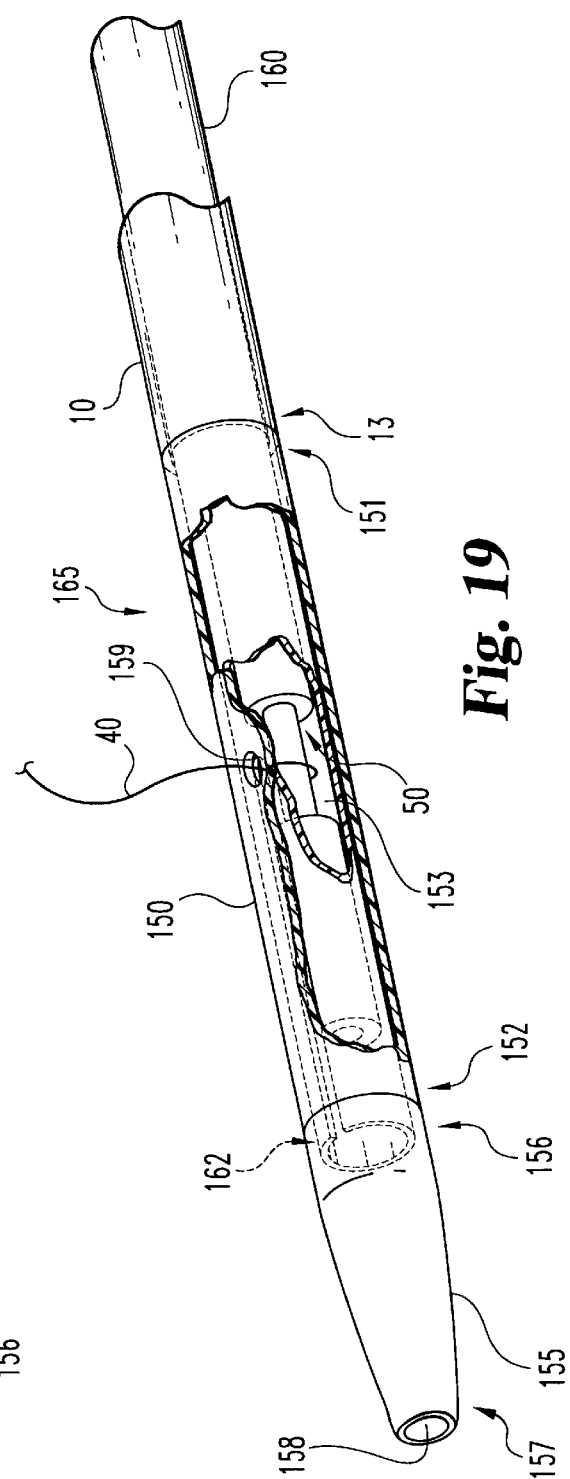

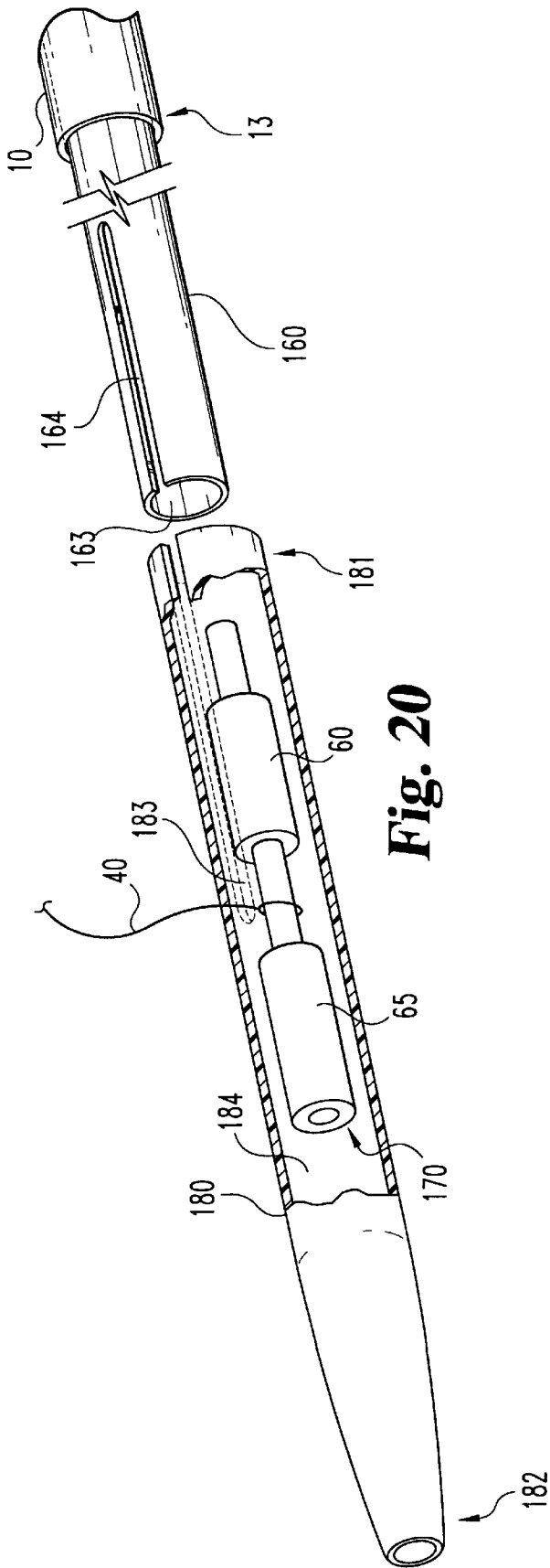
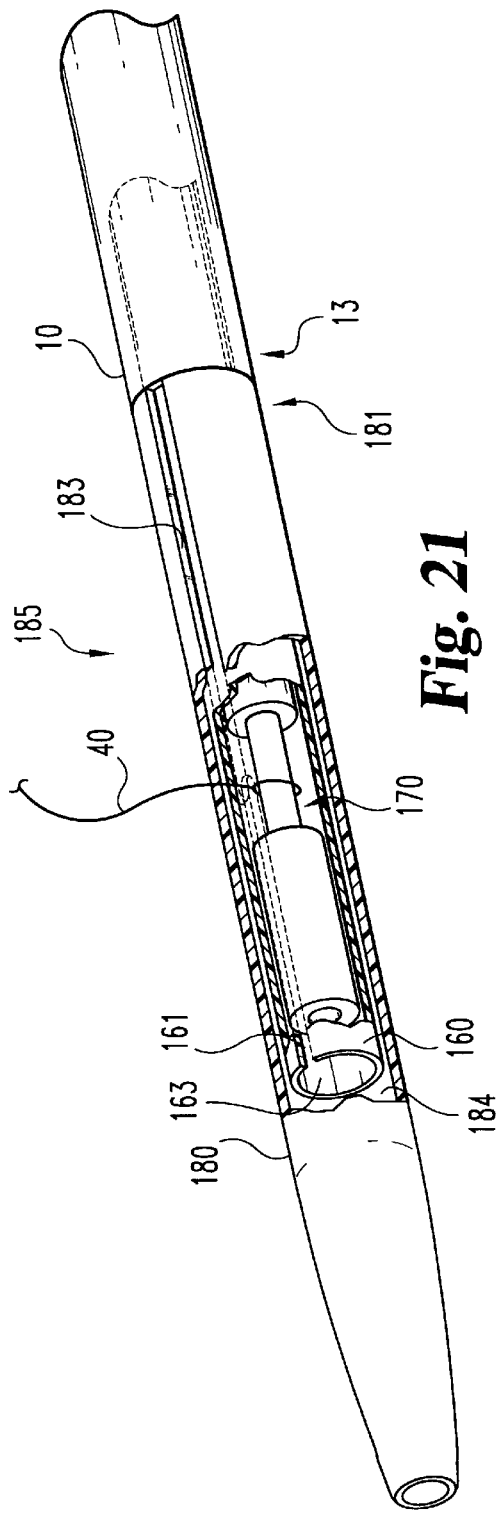

SUTURE ANCHOR DEVICE

FIELD OF THE INVENTION

The present invention relates generally to the field of surgical methods and devices for establishing drains in intra-abdominal viscera.

BACKGROUND OF THE INVENTION

The insertion of a drain tube into the stomach, gall bladder and other intra-abdominal viscera carries an inherent risk of spillage of gastric juices, bile or infected fluids into the peritoneal cavity if the viscus becomes invaginated during tract dilation, or the wire guide becomes coiled within the peritoneal cavity and the drain can not be reinserted. Various devices and methods have been proposed for the purpose of facilitating the insertion of drains in intra-abdominal viscera. Many of these methods utilize an anchor attached to a suture wherein the anchor is inserted into a viscus lumen and the viscus is pulled against a body wall. However, most of these methods require the anchor to be delivered by a relatively large gauge introducer needle as the inside diameter of the needle must be large enough to accommodate the anchor. A potential of injuring the interior of a viscus by the needle point during placement of the anchor exists when such large gauge needles are utilized. A device and method for anchoring a viscus to a body wall of a patient that eliminates the use of large gauge needles and thus reduces the potential of injuring the interior of a viscus by the needle point is needed. The present invention addresses this need.

SUMMARY OF THE INVENTION

The present invention relates to a suture anchor device, a visceral anchor for anchoring a viscus to a body wall, a kit for anchoring a viscus to a body wall and a method for anchoring a viscus to a body wall of a patient.

In one aspect of the invention, a suture anchor device is described that includes a first sheath, a reinforcing member, and a visceral anchor. The first sheath, reinforcing member and anchor all have a proximal end, a distal end and a lumen extending longitudinally therethrough. The reinforcing member is disposed in the lumen of the first sheath and, in one embodiment of the invention, is a cannula. The visceral anchor includes a second sheath wherein the proximal end of the second sheath abuts the distal end of the first sheath. The anchor further includes a suture having a first secured region and a second secured region wherein the first secured region is attached to the anchor. The anchor also includes an attachment member disposed within the lumen of the second sheath. The attachment member is further configured to secure the suture.

In another embodiment of the invention, the visceral anchor may include a second suture. The second suture is advantageous in retrieving the anchor after the anchor is deployed in a viscus lumen.

In a further embodiment, the device includes a first sheath, a reinforcing member and a second sheath all having a proximal end, a distal end and a lumen extending longitudinally therethrough. The device further includes an elongated member disposed in the lumen of the second sheath wherein the elongated member has a proximal end, a distal end and a lumen extending longitudinally therethrough. The device further has a suture having a first secured region and a second secured region. The first secured region is attached to the elongated member. A sleeve may be disposed about, preferably circumferentially about, the elongated member.

In yet another embodiment of the invention, the suture anchor device includes a suture securing means. In one embodiment, the suture securing means is a cap mounted at the proximal end of the first sheath. The cap has a locking slot wherein the second secured region of the suture is positioned in the locking slot.

In a further embodiment of the invention, a visceral anchor for anchoring a viscus to a body wall is provided. The visceral anchor includes a sheath, an attachment member and a suture having opposing ends. The sheath and attachment member are elongated members having a proximal end, a distal end and a lumen extending longitudinally therethrough. In another aspect of the invention, the visceral anchor may include at least one sleeve disposed about the attachment member. One of the opposing ends of the suture is advantageously attached to the anchor, preferably in a central region of the attachment member.

In yet a further aspect of the invention, a kit for anchoring a viscus to a body wall is provided. The kit includes a needle and the suture anchor device described above. The kit may also include a guide preferably a wire guide.

In a further embodiment of the invention, a method for anchoring a viscus to a body wall of a patient is provided. The method includes providing a tract from outside of the body through the skin and the interior viscus wall to a viscus lumen wherein the tract has a longitudinal axis extending from outside the body to the viscus lumen, positioning a suture anchor device described above through the tract and in the viscus lumen, deploying the visceral anchor into the viscus lumen and moving the proximal end of the suture to draw the anchor against the interior wall of the viscus so that the viscus is pulled against a body wall, such as an abdominal wall. In one aspect of the invention, the method includes puncturing the skin with a needle having a lumen to provide a tract from outside of the body through the skin and interior viscus to the viscus lumen. A wire preferably a micro guide may then be inserted through the lumen of the needle and into the viscus lumen. The needle may then be removed prior to positioning the suture anchor device.

It is an object of the invention to provide a suture anchor device that may deploy a visceral anchor without loading the anchor into a lumen of a large gauge needle, thus reducing the probability of injuring the interior of a viscus.

It is a further object of the invention to provide a suture anchor that does not need to be loaded into a needle for delivery into a viscus lumen and thus reduces the probability of injuring the interior of a viscus.

It is yet another object of the invention to provide a kit for anchoring a viscus to a body wall that includes a suture anchor device that may deploy a visceral anchor wherein the probability of injuring the interior of a viscus is reduced.

It is a further object of the invention to provide a method for anchoring a viscus to a body wall that reduces the probability of injuring the interior of a viscus.

These and other objects and advantages of the present invention will become apparent after reading the following description of the preferred embodiment.

BRIEF DESCRIPTION OF THE FIGURES

FIG. 1 is a side view of a suture anchor device of the present invention with a portion of a sheath component broken away to show a reinforcing member component.

FIG. 2 is a side perspective view of the sheath component of a suture anchor device of the present invention FIG. 3 is a side perspective view of the reinforcing member.

FIG. 4 is a side perspective view of a visceral anchor component of the suture anchor device.

FIG. 18 is a side perspective view of an alternate embodiment of a visceral anchor and reinforcing member component of a suture anchor device of the present invention.

FIG. 19 is a side perspective view of a distal portion of a suture anchor device formed from assembling the components shown in FIG. 18.

FIG. 20 is a side perspective view of another alternate embodiment of a visceral anchor and reinforcing member component of a suture anchor device of the present invention.

FIG. 21 is a side perspective view of a distal portion of a suture anchor device formed from assembling the components shown in FIG. 20.

DESCRIPTION OF THE PREFERRED EMBODIMENTS

Figure 5:
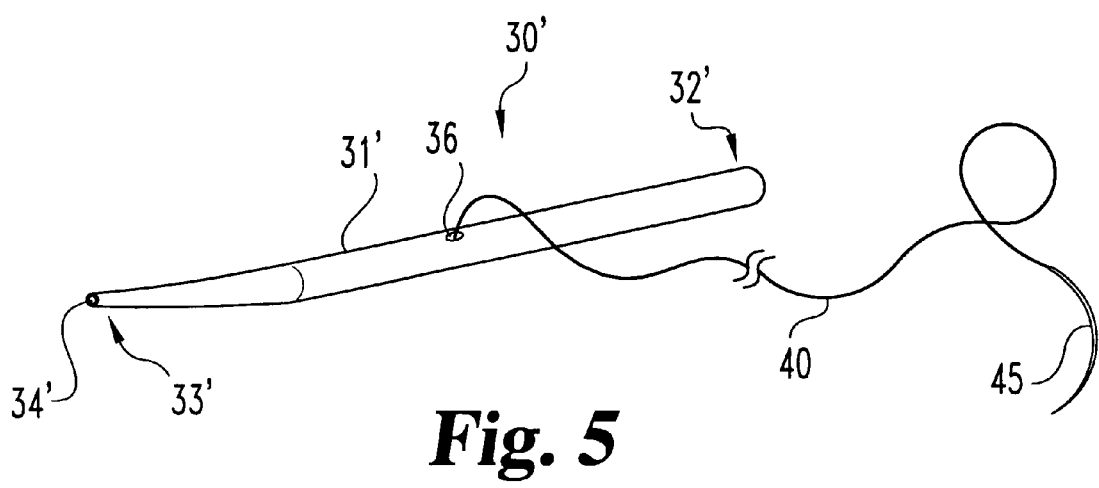
FIG. 5 is a side perspective view of a visceral anchor component of the suture anchor device having a curved distal end.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As described above, the present invention relates to a suture anchor device, a visceral anchor for anchoring a viscus to a body wall, a kit for anchoring a viscus to a body wall and a method for anchoring a viscus to a body wall of a patient. The device deploys a visceral anchor that anchors a viscus to a body wall so that fluids from intra-abdominal viscera do not spill into the peritoneal cavity during draining procedures. Referring to FIGS. 1–4, one embodiment of a suture anchor device is shown. Suture anchor device 1 includes sheath 10, reinforcing member 20 and anchor 30 with attached suture 40. Device 1 may also include a suture securing means, including cap 80 having locking slot 83. As best seen in FIG. 2, sheath 10 is an elongated member 11 having a proximal end 12 and a distal end 13. Lumen 14 extends longitudinally through sheath 10. Sheath 10 is advantageously constructed from a flexible material as known in the art, including polyethylene, polyurethane, nylon, polytetrafluoroethylene (Teflon) or a combination thereof, but is preferably constructed from polytetrafluoroethylene. The inside and outside diameters and length of sheath 10 may be chosen by one skilled in the art depending on the situation. However, the inside diameter of sheath 10 is advantageously about 1.0 mm (3 French) whereas the outside diameter is advantageously about 1.67 mm (5 French). The length of sheath 10 is typically about 15 cm.

Turning now to FIG. 3, reinforcing member 20 includes an elongated member 21 that has a proximal end 22, a distal end 23, and a lumen 24 extending longitudinally therethrough. Reinforcing member 20 is preferably a cannula and is advantageously made from materials as known in the art, including metals such as stainless steel, Nitinol and Inconel. However, reinforcing member 20 is preferably made from stainless steel. A luer-lock fitting 25 as known in the art is mounted on proximal end 22 of reinforcing member 20 and communicates with lumen 24. The inside and outside diameter of reinforcing member 20 and its length may be chosen by one skilled in the art depending on the situation. However, the inside diameter of reinforcing member 20 is typically about 0.025 in and the outside diameter is typically about 0.035 in (20 gauge). Moreover, the length of reinforcing member 20 is advantageously about 18 cm.

Figure 6:
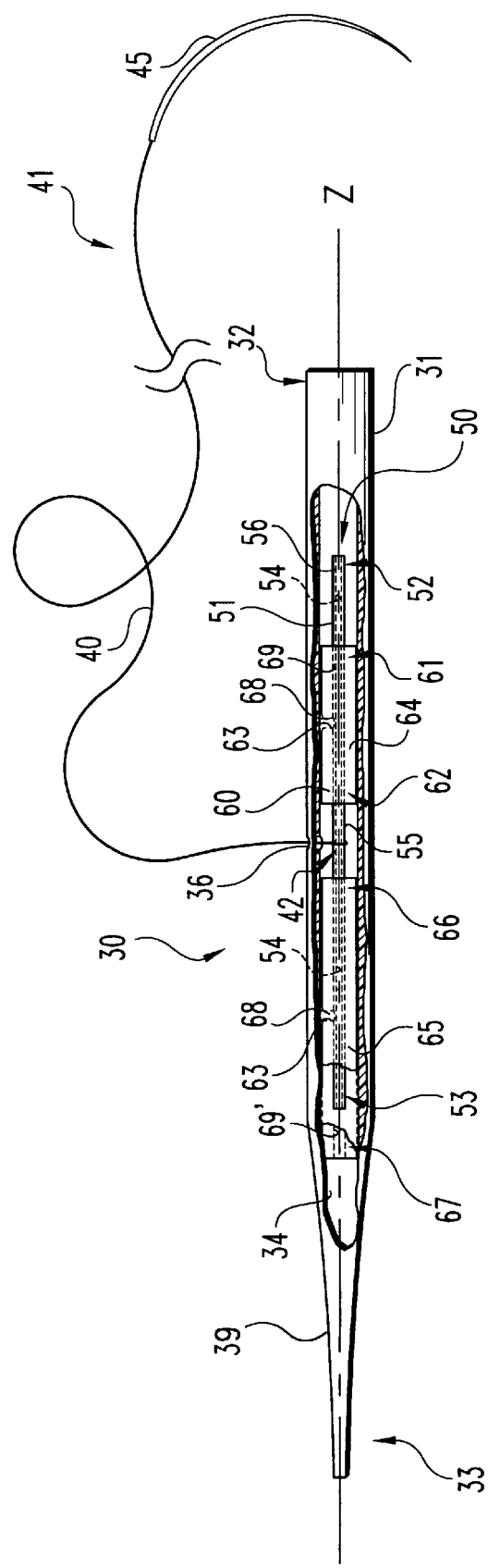
FIG. 6 is a cut-away side view of the anchor shown in FIG. 4.

Turning now to FIG. 4, visceral anchor 30 includes a sheath 31 that is an elongated member that is advantageously constructed from the same material as sheath 10. Sheath 31 includes a proximal end 32, a distal end 33 and a lumen 34 extending longitudinally therethrough. The diameter of the sheath may be uniform along its length. However, it is preferred that distal end 33 of sheath 31 is configured for entering a passageway in a body made by incising a region of the body. For example, distal end 33 of sheath 31 is preferably tapered to precisely fit the micro wire guide and may have other configurations as known in the art, such as a pyramidal (3 or 4 sided, for example) or conical. The taper may be elongated to 1 cm or longer to facilitate entry into the patient. Further, the tapered end may be circular or polygonal in cross section. Distal end 33 may also be either straight as shown in FIG. 4 or curved as shown in FIG. 5. A curved end may be useful in making it easier to insert the suture anchor device through a puncture made in the patient's body and makes the tapered end of the anchor less traumatic to the interior of the viscera. The extent of the curvature may vary, but the angle of curvature between distal end 33' of visceral anchor 30' and the central longitudinal axis of the anchor is preferably about 25°. The length of sheath 31 may vary but is advantageously about 3.5 cm. Visceral anchor 30' also includes sheath 31' having proximal end 32' and lumen 34' extending longitudinally therethrough. It is further preferred that sheath 31 have aperture 36 that is configured for passage of suture 40. Aperture 30 is advantageously located at a point equidistant from proximal end 32 and distal end 33 of sheath 31. The diameter of aperture 36 may be chosen as one skilled in the art would appreciate, but is advantageously about 0.9 mm (0.035 in). Visceral anchor 30 further includes an attachment member 50 disposed in lumen 34 of sheath 31 as seen in FIG. 6. It is noted here that the same numerical designations for various elements depicted in FIG. 5 refer to the same elements as detailed in FIG. 4.

Referring to FIG. 6, it is seen that attachment member 50 includes an elongated member 51 having a proximal end 52, a distal end 53, a lumen 54 extending longitudinally therethrough and a central region 55. In a preferred embodiment, attachment member 50 preferably has at least one sleeve 60 disposed about elongated member 51 that is advantageously manufactured from the same material as reinforcing member 20. Sleeve 60 is an elongated member that may be advantageously disposed circumferentially about elongated member 51 and may be secured to elongated member 51 by methods known in the art, including soldering and use of adhesives. If sleeve 60 is secured to elongated member 51 with solder 68, it is preferable that sleeve 60 is secured to elongated member 51 by making a thru-hole 63 that extends from outer surface 64 of sleeve 60 into lumen 69 (defined by the inner surface of the sleeve) of sleeve 60 and soldering sleeve 60 to outer surface 56 of elongated member 51 in the region of thru-hole 63. Thru-hole 63 may be circular or have any other shape that will allow solder 68 to contact both outer surface 56 of elongated member 51 and sleeve 60 to secure the sleeve to the elongated member. Thru-hole 63 is further preferably made in a central region of sleeve 60 equidistant from proximal end 61 and distal end 62 of sleeve 60. Moreover, the diameter of thru-hole 63 may be chosen by one skilled in the art after reading this disclosure but is advantageously about 0.025 in. The length of sleeve 60 may vary as one skilled in the art would appreciate but is advantageously about 1 cm. In this embodiment, distal end 62 of sleeve 60 may be placed any distance, as one skilled in the art would appreciate, from distal end 33 of sheath 31. However, distal end 62 of sleeve 60 is advantageously about 1.5 cm from distal end 33 of sheath 31. In a further preferred embodiment, a second sleeve 65, an elongated member having lumen 69' defined by the inner surface of the sleeve, is disposed about, preferably circumferentially around, elongated member 51 and is in spaced relation with sleeve 60. That is, sleeves 60 and 65 are preferably longitudinally aligned about longitudinal axis Z of elongated member 51. Sleeve 65 may also have a thru-hole 63 so that sleeve 65 may be secured to outer surface 56 of elongated member 51 with solder 68. Sleeve 65 is further preferably disposed about distal end 53 of elongated member 51 and further preferably extends past the distal end of elongated member 51. However, distal end 67 of sleeve 65 may be aligned with distal end 53 of elongated member 51 or may be proximal to distal end 53 of elongated member 51 as one skilled in the art would appreciate. The length of sleeve 65 may vary as one skilled in the art would appreciate. However, the length of sleeve 65 is advantageously about 7 mm to about 8 mm.

Figure 9:
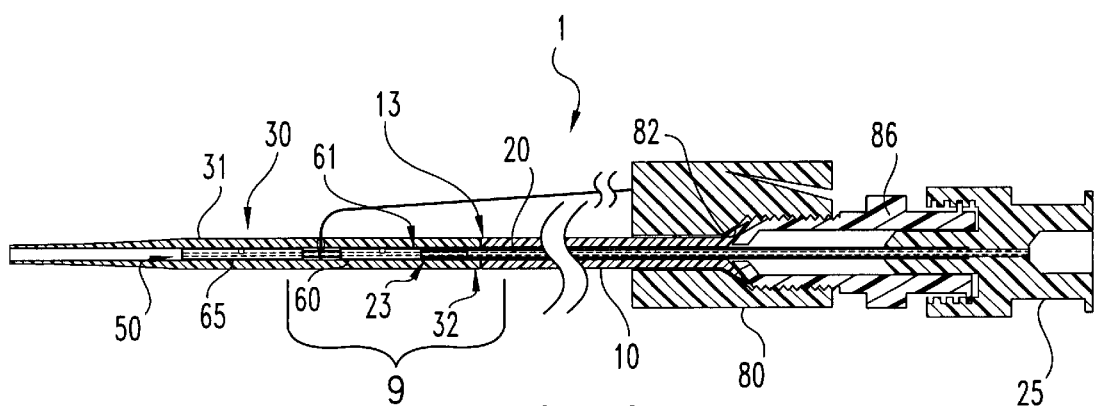
FIG. 9 shows a longitudinal cross-section view of the suture anchor device shown in FIG. 8 viewed along line 8—8.
Figure 10:
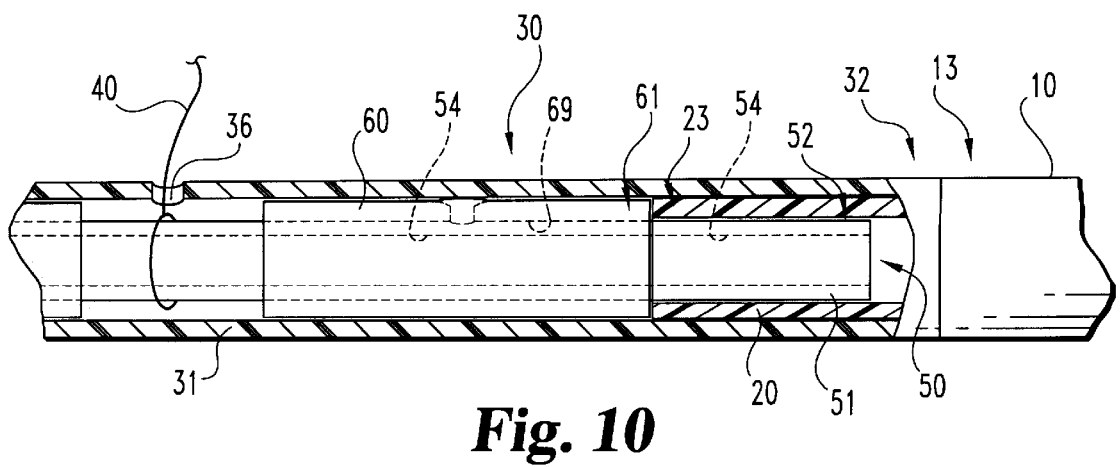
FIG. 10 depicts region 9 of the suture anchor device shown in FIG. 9, showing the telescopic engagement of attachment member 50 and reinforcing member 20.

Sleeves 60 and 65 preferably function to limit the distance that distal end 23 of reinforcing member 20 travels over proximal end 52 of elongated member 51 when forming a telescopic joint as more fully explained below with reference to FIGS. 9 and 10. Moreover, in certain embodiments, the sleeves may increase the outer diameter of attachment member 50 so it will fit snugly within sheath 31.

In yet another embodiment, the outside diameter of attachment member 50 may be such that it is held securely in place within lumen 34 of sheath 31, without the need for sleeves 60 or 65. In this embodiment, an annular extension of the inner surface of attachment member 50 or a ring snugly disposed within lumen 54 may act to limit the distance that distal end 23 of reinforcing member 20 travels in lumen 54 of elongated member 51, thus limiting the depth of the telescopic joint.

Continuing to refer to FIG. 6, distal end 42 of suture 40 may be attached to sheath 31 but is preferably attached to elongated member 51, typically in central region 55 and further preferably at a location within central region 55 that is equidistant from proximal end 66 of sleeve 65 and distal end 62 of sleeve 60. Suture 40 may then extend transversely from longitudinal axis Z through sheath 31, preferably from lumen 34 through outer surface 39 of sheath 31. The length of central region 55 may vary but is typically about 1 mm. In one embodiment as best seen in FIG. 1, a region 43 of suture 40 may be advantageously secured to a suture securing means as described below. Region 43 of suture 40 is preferably located on suture 40 a distance proximal from distal end 42 that approximates the distance between aperture 36, where suture 40 emerges, to the suture securing means. Moreover, proximal end 41 of suture 40 may be attached to a suture needle 45 which is advantageous in securing proximal end 41 of the suture to a patient's skin as described below.

Figure 7:
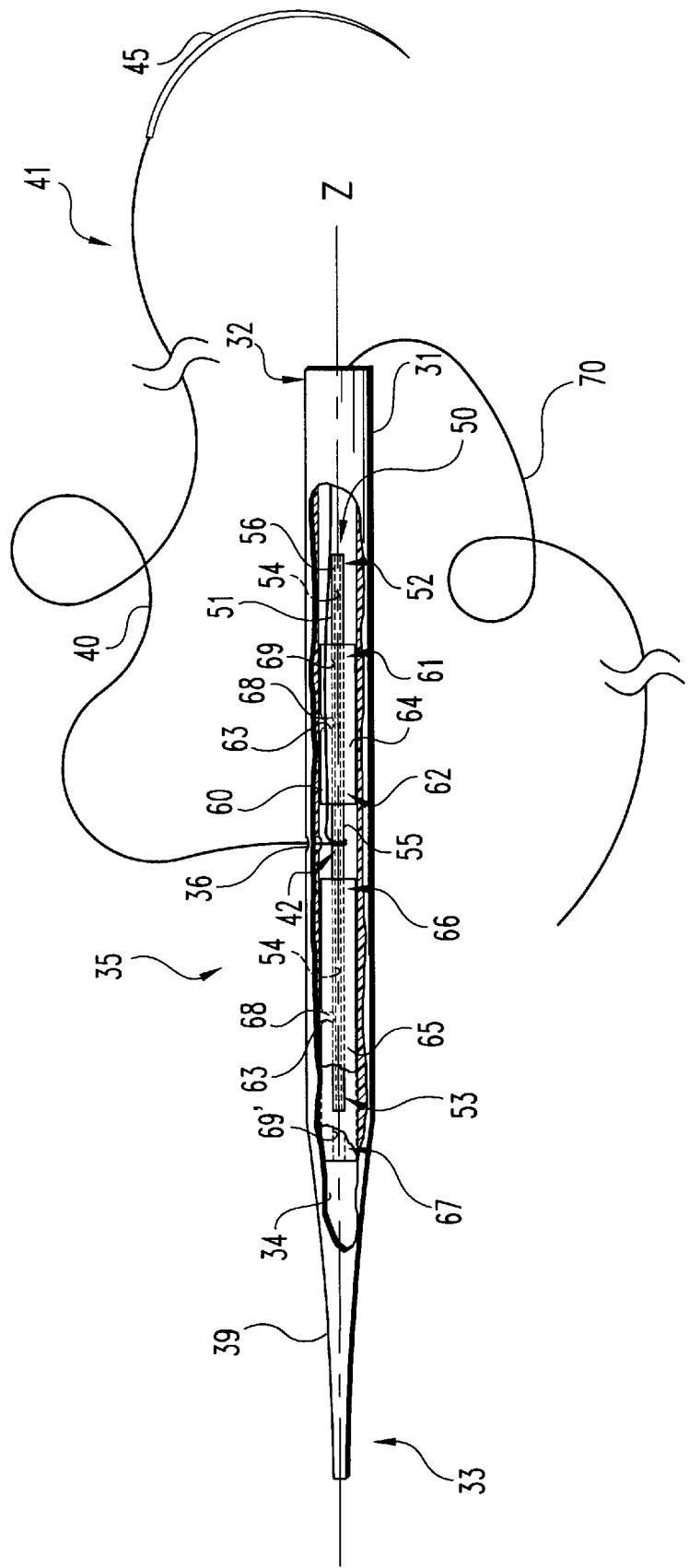
FIG. 7 is a side view of the anchor shown in FIG. 5 with a second suture.

In yet another embodiment of the visceral anchor shown in FIG. 7, a second suture 70 may be secured to attachment member 50, preferably in central region 55, and advantageously protrudes through proximal end 32 of sheath 31 of the visceral anchor to form visceral anchor 35. However, suture 70 may also protrude through distal end 33 of sheath 31. Visceral anchor 35, in such embodiments, may be retrieved after it has been deployed in a patient's body as described below. It is noted here that the same numerical designations for various elements depicted in FIG. 7 refer to the same elements as detailed in FIG. 6.

Figure 8:
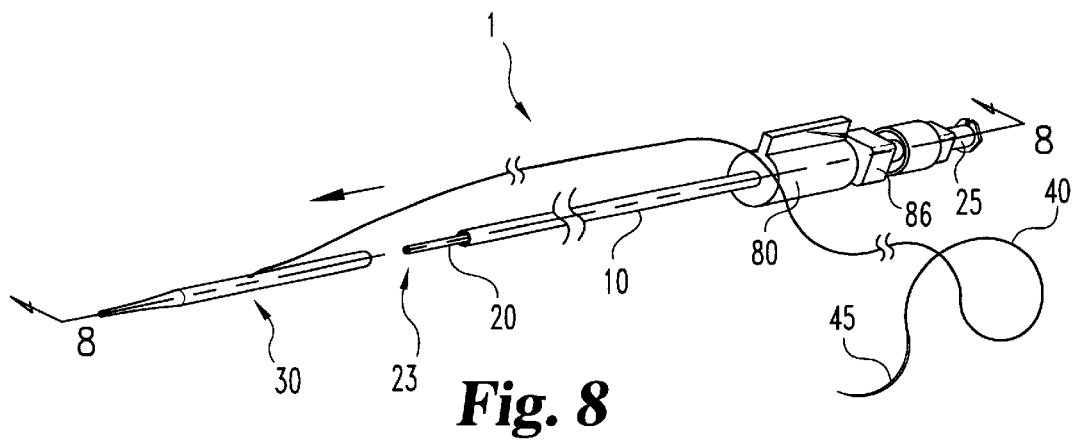
FIG. 8 is a side perspective view showing a reinforcing member component of the present invention disposed in the lumen of the sheath component and showing how a visceral anchor component is attached to form a suture anchor device of the present invention.

As best seen in FIGS. 1 and 2, the suture securing means may be a cap 80 having a locking slot 83. The cap may be attached to sheath 10 at proximal end 12 and communicates with lumen 14. Cap 80 has an outer surface 81 and inner surface 82 (as seen in FIG. 8). Locking slot 83 is advantageously disposed on outer surface 81 of cap 80. Locking slot 83 may include an extension 84 of cap 80, such as a substantially rectangular extension, that is preferably longitudinally disposed along cap 80 and a gap 85 that preferably extends along the length of extension 84. However, extension 84 may assume other shapes as known in the art, including spherical, pyramidal and other polygonal shapes. Locking slot 83 is configured to secure a second secured region 43 of suture 40. Inner surface 82 of cap 80 is advantageously configured to threadingly receive a luer-lock fitting 86 as known in the art. Luer-lock fitting 86 advantageously communicates with lumen 14 of sheath 10. An adhesive as known in the art may also be used to secure luer-lock fitting 86. Another suture securing means that may be used includes the combination of a cotton pledger, washer and crimpable elements as described in U.S. Pat. No.

5,531,678 which is hereby incorporated by reference. Other suture securing means as known in the art may be used, including elastic bands and use of tape.

Referring to FIG. 8, in order to assemble a suture anchor device, reinforcing member 20 is disposed in lumen 14 (seen in FIG. 2) of sheath 10 by inserting distal end 23 of reinforcing member 20 into lumen 14 of sheath 10 and advancing the reinforcing member until luer-lock fittings 25 and 86 contact each other. Luer-lock fitting 25 is then threadedly secured to luer-lock fitting 86. Visceral anchor 30 is then attached to sheath 10 by telescopingly engaging attachment member 50 and reinforcing member 20 to form suture anchor device 1 as seen in FIG. 9 That is, visceral anchor 30 is attached to sheath 10 by disposing distal end 23 of reinforcing member 20 over proximal end 52 of 30 elongated member 51 of attachment member 50. When assembled, distal end 23 of reinforcing member 20 abuts proximal end 61 of sleeve 60 whereas proximal end 32 of sheath 31 abuts distal end 13 of sheath 10, as best seen in enlarged region 9 of FIG. 9 shown in FIG. 10. When visceral anchor 30 is secured to sheath 10, the combination of sheath 31 of visceral anchor 30 and sheath 10 may function as a dilator wherein a distal segment of the dilator is the visceral anchor.

In yet another embodiment of the present invention, a kit for anchoring a viscus to a body wall is provided. The kit includes the suture anchor device described above as well as a needle, such as a 21 gauge needle having a length of about 15 cm. The kit may further include a micro wire guide. The diameter of the wire guide is preferably about 0.018 in. The components of the kit may be packaged in a sterile manner in packaging as known in the art.

Figure 11:
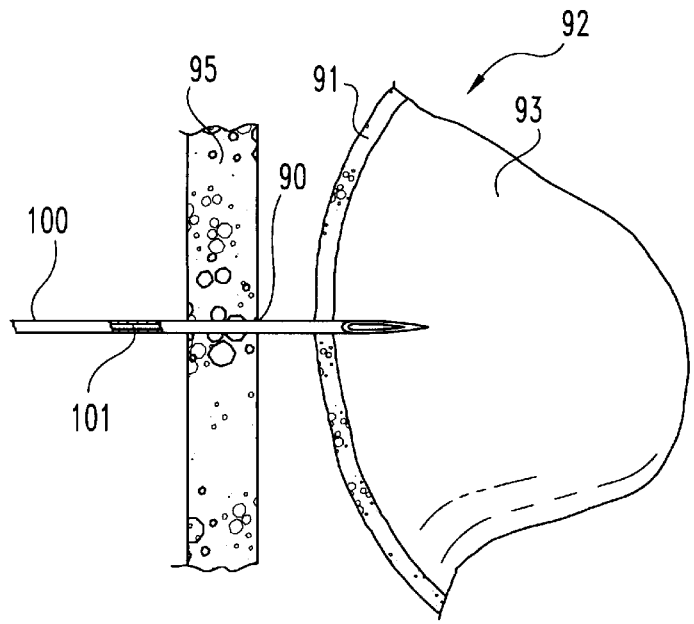
FIG. 11 is a schematic representation of a step in one embodiment of the method of visceral wall mobilization of the present invention.

The method of visceral wall mobilization utilizing the suture anchor device of the present invention is illustrated in FIGS. 11–15. Referring to FIG. 11, a tract or passageway 90 is advantageously established from outside the body through the skin and viscus wall 91 of viscus 92 to the viscus lumen 93 by a needle puncture. Needle 100 is advantageously a small gauge needle as known in the art, such as 21 gauge and is typically about 15 cm long. The gauge of the needle is smaller than needles typically utilized in such a procedure as it is not necessary in the procedure herein described to insert the visceral anchor through the needle as will be explained below.

Figure 12:
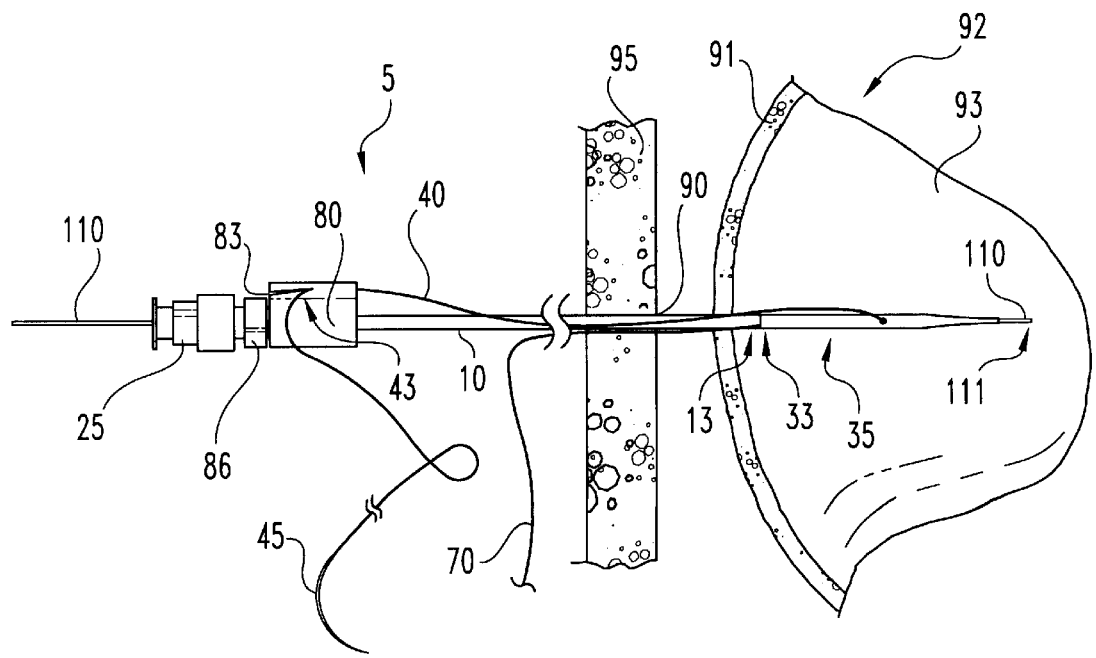
FIG. 12 is a schematic representation of a further step of the method of FIG. 11, particularly showing a visceral anchor component of a suture anchor device after insertion into a hollow viscus.

After needle 100 enters and thereby locates the distended viscus lumen 93, a soft-tipped wire guide 110 is advanced through lumen 101 of needle 100. Needle 100 can then be removed and suture anchor device 5 may be advanced over wire guide 110 until the entire length of visceral anchor 35 is contained within viscus lumen 93 as shown in FIG. 12. Suture anchor device 5 is identical to device 1 except that device 5 includes retrievable visceral anchor 35, not visceral anchor 30.

Figure 13:
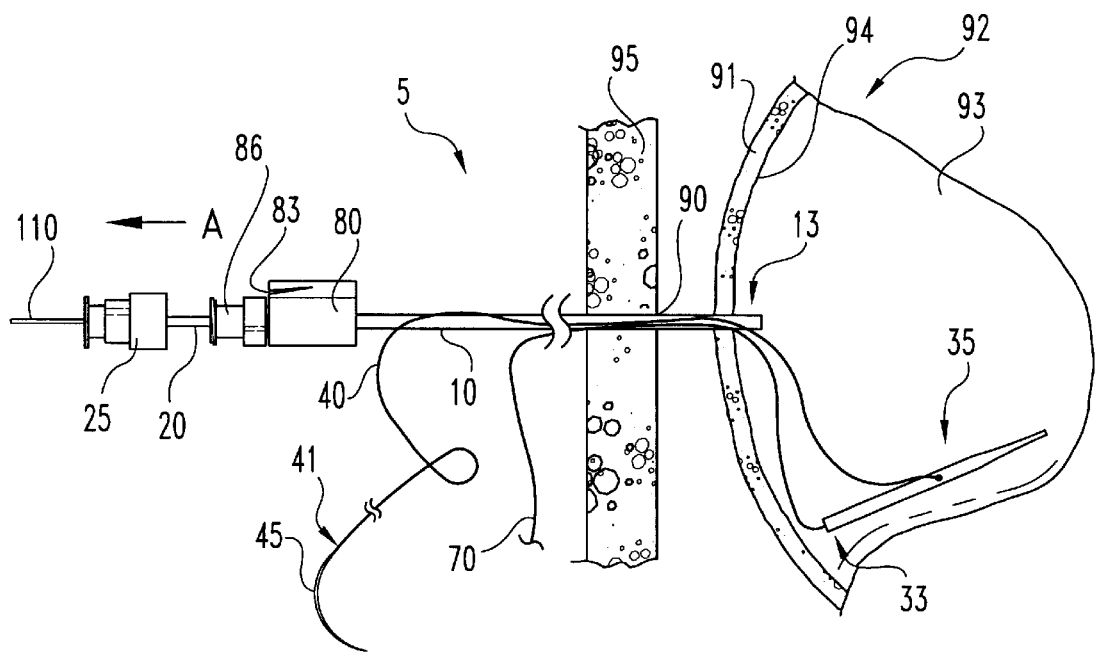
FIG. 13 is a schematic representation of a further step of the method of FIG. 12, showing deployment of a visceral anchor component of a suture anchor device into the lumen of a hollow viscus.

Referring to FIG. 13, to deploy visceral anchor 35 into viscus lumen 93, reinforcing member 20 must be translationally moved in the general proximal direction indicated by arrow A. Moreover, if suture 40 is secured to device 5, it must be unsecured. For example, if a region 43 of suture 40 is secured to locking slot 83 of cap 80, it must be removed from the slot. It must also be noted that wire guide 110 should be moved, in the general proximal direction indicated by arrow A, so that its distal end 111 clears the region of the device where proximal end 33 of visceral anchor 35 abuts distal end 13 of sheath 10 so that visceral anchor 35 can be deployed.

Figure 14:
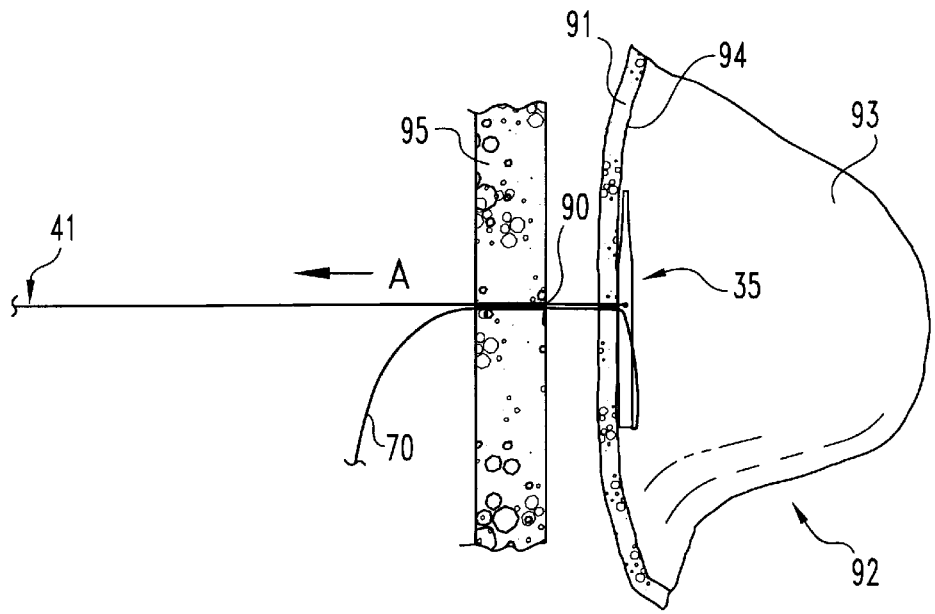
FIG. 14 is a schematic representation of a further step according to the method of FIG. 13, particularly showing a visceral anchor positioned in perpendicular relation to the longitudinal axis of the tract and engaged with the viscus wall.
Figure 15:
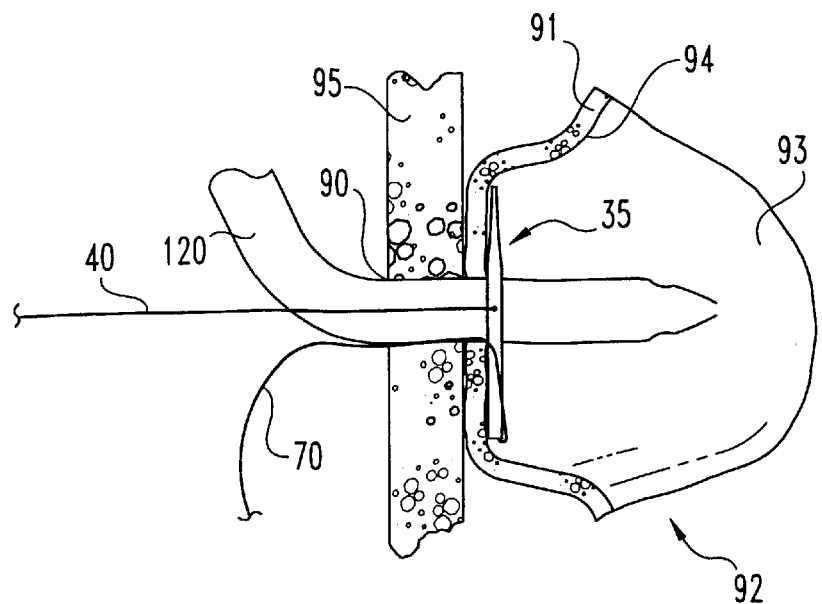
FIG. 15 is a schematic representation of another step according to the method of FIG. 14, particularly showing the viscus wall retracted against a body wall, such as an abdominal wall, and a drain tube inserted into the viscus lumen.

Once visceral anchor 35 is deployed, proximal end 41 of suture 40 is grasped and suture 40 is pulled in the general direction indicated by arrow A which causes visceral anchor 35 to be positioned in perpendicular relation to the longitudinal axis of the tract and which further causes visceral anchor 35 to engage internal wall 94 of viscus 92 as depicted in FIG. 14. Further pulling or traction is exerted on suture 40 in the general proximal direction indicated by arrow A until viscus wall 91 is moved into close approximation to body wall 95, such as the abdominal wall or other parietal wall, as seen in FIG. 15. With viscus wall 91 firmly retracted against body wall 95, there is little chance of intraperitoneal leakage. Tension on suture 40 is maintained by securing suture 40 to the skin by methods known in the art, including use of suture needle 45 at proximal end 41 of suture 40.

If necessary, wire guide 110 can be used to further dilate tract 90 by pushing one or more increasingly larger dilators over the wire guide and into viscus lumen 93. Such dilators are commercially available and therefore have not been shown herein. Drain tube 120 may then be inserted to provide communication between viscus lumen 93 and the outside of the body as seen in FIG. 15.

Figure 16:
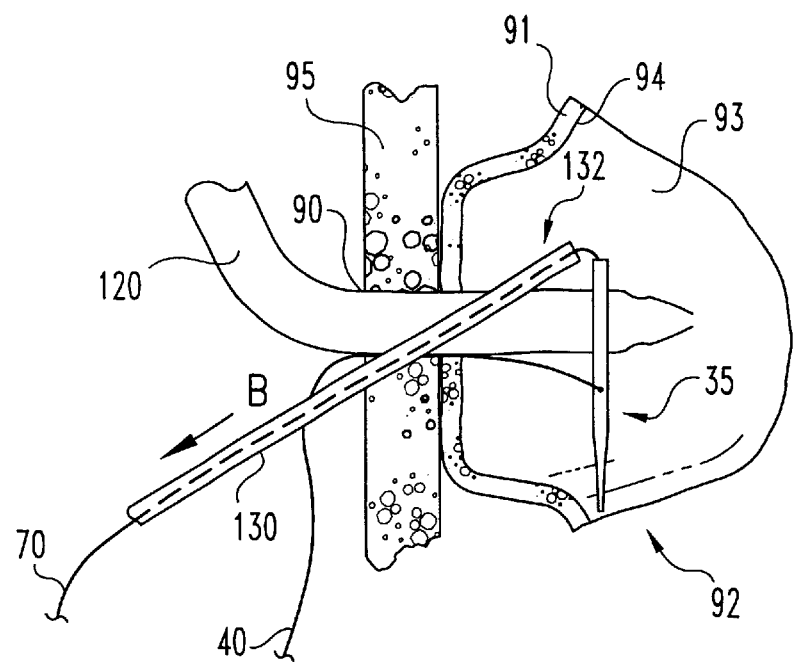
FIG. 16 is a schematic representation according to one embodiment of a visceral anchor removal step of the method of the present invention, particularly showing the visceral anchor released from engagement with the viscus wall and suture 70 extending through a cannula.
Figure 17:
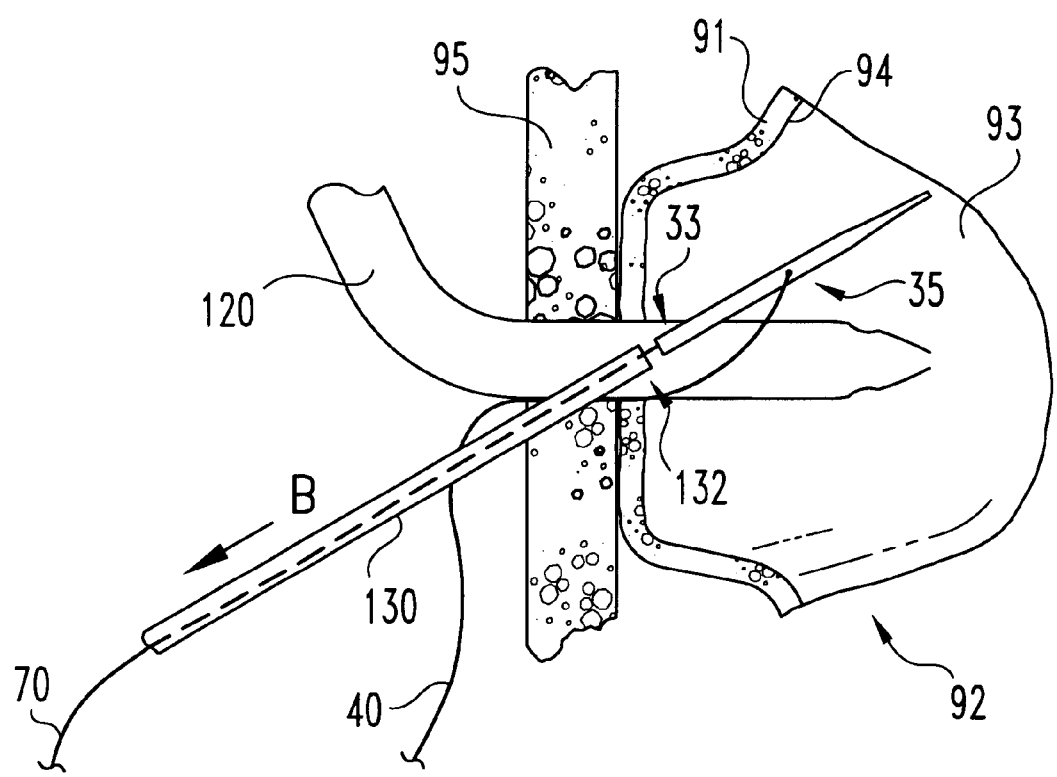
FIG. 17 is a schematic representation according to the anchor removal step of FIG. 16, particularly showing the visceral anchor aligned along the longitudinal axis of a cannula prior to being removed with the cannula.

When the drain tract has been established, visceral anchor 35 may no longer be necessary. One method of retrieving visceral anchor 35 is depicted in FIGS. 16 and 17. Suture 40 is cut, thus releasing the tension on visceral anchor 35. A cannula 130 as known in the art, such as a cannula having an inside diameter of about 0.052 in and an outside diameter of about 0.065 in (16 gauge), is then threaded over suture 70 as shown in FIG. 16 and inserted alongside drain tube 120 back into viscus lumen 93. Once distal end 132 of cannula 130 is inside viscus lumen 93, a gentle force in the general direction of arrow B may be applied on suture 70. Visceral anchor 35 will realign itself along the longitudinal axis of cannula 130 as shown in FIG. 17 and can then be easily withdrawn along with cannula 130. Proximal end 33 of anchor 35 is held in contact with distal end 132 of cannula 130 by applying tension on suture 70, thereby maintaining coaxial alignment during withdrawal of cannula 130 and anchor 35. Suture 40 will trail visceral anchor 35 as the visceral anchor and the cannula are withdrawn.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, FIGS. 18 and 19 show an alternative embodiment of a visceral anchor component of the present invention. Visceral anchor 140 includes attachment member 50 and sheath 150. Sheath 150 is an elongated member wherein the outer diameter of sheath 150 is preferably uniform along the length of the sheath. Proximal end 156 of distal tip 155 preferably abuts distal end 152 of sheath 150. Distal tip 155 is an elongated element that is advantageously tapered at its distal end 157 to fit the micro guide wire. In this embodiment, distal tip 155 may have a smaller inside diameter than in the other embodiments described such that distal end 162 of reinforcing member 160 may telescopingly engage distal tip 155. That is, upon forming suture anchor device 165, a distal portion of which is shown in FIG. 19, distal end 162 of reinforcing member 160 is disposed through lumen 153 of sheath 150 and inside lumen 158 of distal tip 155 as seen in FIG. 19. In this embodiment, reinforcing member 160 is identical to reinforcing member 20 except that it preferably has an elongated slot 164 or similar opening as best seen in FIG. 18 so that suture 40 may extend through the slot and through aperture 159 of sheath 150. It is further seen in FIG. 19 that distal end 13 of sheath 10 abuts proximal end 151 of sheath 150. When such an anchor is deployed by proximal movement of reinforcing member 160 as described above, distal tip 155 separates from visceral anchor 140. If such an anchor is used for anchoring of the stomach to the abdominal wall, distal tip 155 may be removed from the stomach by passage through the intestinal tract after the anchor is deployed. Alternatively, distal tip 155 may be formed from a bioabsorbable component as known in the art, such as polyglycolic acid.

In yet another embodiment depicted in FIGS. 20 and 21, visceral anchor 170 includes the same attachment member 50 with attached suture 40 that is shown in FIGS. 6 and 7. In this embodiment, visceral anchor 170 is disposed in lumen 184 of sheath 180 having proximal end 181 and distal end 182. As seen in FIG. 21, when forming suture anchor device 185, a distal portion of which is shown, reinforcing member 160 is disposed in lumen 184 of sheath 180, circumferentially about visceral anchor 170. That is, visceral anchor 170 is disposed in lumen 163 of reinforcing member 160. The diameter of sleeves 60 and 65 are chosen such that, when reinforcing member 160 is translationally moved to deploy visceral anchor 170, sheath 180 will fall away from visceral anchor 170. It is also seen in this embodiment that both reinforcing member 160 and sheath 180 are identical to reinforcing member 20 and sheath 31 in all respects except that they preferably have an elongated slot (or similar opening) 164 and 183, respectively, in order to allow suture 40 to extend through the slot. It is further noted that the outside diameter of reinforcing member 160 should be chosen such that it will be large enough to fit snugly in lumen 184 of sheath 180 in order to retain sheath 180. It is to be noted here that distal end 182 of sheath 180 and distal end 157 of distal tip 155 may have any of the configurations as described above for the distal end of visceral anchors 30 and 30'.

What is claimed is:

1. A suture anchor device, comprising:
   a first sheath having a proximal end, a distal end and a lumen extending longitudinally therethrough;
   a reinforcing member having a proximal end, a distal end and a lumen extending longitudinally therethrough, said reinforcing member disposed in said lumen of said first sheath; and
   a visceral anchor comprising:
      a second sheath having a proximal end, a distal end and a lumen extending longitudinally therethrough, said proximal end of said second sheath abutting said distal end of said first sheath;
      a suture having a first secured region and a second secured region, the first secured region being attached to said anchor; and
      an attachment member disposed within said lumen of said second sheath and configured to secure said suture.

2. The device of claim 1, wherein said suture has a proximal end and a distal end, said proximal end attached to a suture needle and said distal end being said first secured region.

3. The device of claim 1, wherein said device further comprises a suture securing means.

4. The device of claim 3, wherein said suture securing means comprises a cap disposed at said proximal end of said first sheath, said cap having a locking slot.

5. The device of claim 4, wherein said first secured region of said suture is positioned in said locking slot.

6. The device of claim 1 wherein said attachment member comprises an elongated member having a proximal end, a distal end and a lumen extending longitudinally therethrough.

7. The device of claim 6, wherein said attachment member comprises a first sleeve disposed about said elongated member.

8. The device of claim 7, wherein said first sleeve is disposed circumferentially about said elongated member.

9. The device of claim 7, wherein said attachment member comprises a second sleeve disposed about said elongated member in spaced relation to said first sleeve.

10. The device of claim 9, wherein said second sleeve is disposed circumferentially around said elongated member.

11. The device of claim 1, wherein said reinforcing member and said attachment member of said anchor are telescopingly engaged.

12. The device of claim 1, wherein said distal end of said second sheath is tapered.

13. The device of claim 12, wherein said distal end of said second sheath is conical.

14. A suture anchor device, comprising:
   a first sheath having a proximal end, a distal end and a lumen extending longitudinally therethrough;
   a reinforcing member having a proximal end, a distal end and a lumen extending longitudinally therethrough, said reinforcing member disposed in said lumen of said first sheath;
   a cap mounted at said proximal end of said first sheath, said cap having a locking slot; and
   a visceral anchor comprising:
   a second sheath having a proximal end, a distal end and a lumen extending longitudinally therethrough, said proximal end of said second sheath abutting said distal end of said first sheath; and
   a suture having a first secured region and a second secured region, the first secured region being a distal end of said suture attached to said anchor.

15. A suture anchor device, comprising:
   a first sheath having a proximal end, a distal end and a lumen extending longitudinally therethrough;
   a cannula having a proximal end, a distal end and a lumen extending longitudinally therethrough, said cannula disposed in said lumen of said first sheath; and
   a visceral anchor comprising:
      a second sheath having a proximal end, a distal end and a lumen extending longitudinally therethrough, said proximal end of said second sheath abutting said distal end of said first sheath;
      a suture having a first secured region and a second secured region, said first secured region being attached to said anchor; and
      an attachment member disposed within said lumen of said second sheath and configured to secure said suture.

16. The device of claim 15, said device further comprising a suture securing means.

17. the device of claim 16, wherein said suture securing means comprises a cap mounted at said proximal end of said first sheath, said cap having a locking slot.

18. The device of claim 17, wherein said second secured region of said suture is positioned in said locking slot.

19. The device of claim 15, wherein translational movement of said cannula relative to said first sheath results in deployment of said anchor.

20. The device of claim 15, wherein said distal end of said second sheath is tapered.

21. The device of claim 20, wherein said distal end of said second sheath is conical.

22. A suture anchor device, comprising:
a first sheath having a proximal end, a distal end and a lumen extending longitudinally therethrough;
a reinforcing member having a proximal end, a distal end and a lumen extending longitudinally therethrough, said reinforcing member disposed in said lumen of said first sheath;
a second sheath having a proximal end, a distal end and a lumen extending longitudinally therethrough, said proximal end of said second sheath abutting said distal end of said first sheath;
an elongated member disposed in said lumen of said second sheath, said elongated member having a proximal end, a distal end and a lumen extending longitudinally therethrough; and
a suture having a first secured region and a second secured region, said first secured region being attached to said elongated member.

23. A visceral anchor for anchoring a viscus to a body wall, comprising:
a sheath having a proximal end, a distal end and a lumen extending longitudinally therethrough;
an attachment member including an elongated member having a proximal end, a distal end and a lumen extending longitudinally therethrough, said attachment member disposed in said lumen of said sheath; and
a suture having opposing ends, one of said opposing ends attached to said anchor.

24. The anchor of claim 23, said anchor further comprising at least one sleeve disposed about said elongated member.

25. The anchor of claim 23, wherein said attachment member comprises two sleeves disposed about said elongated member.

26. The anchor of claim 23, wherein the other of said opposite ends of said suture is attached to a suture needle.

27. The anchor of claim 23, wherein said distal end of said sheath is configured for entering a passageway in a body made by puncturing a region of said body.

28. The anchor of claim 23, wherein said distal end of said sheath is tapered.

29. The anchor of claim 23, wherein said one of said opposing ends is attached to said attachment member.

30. A visceral anchor, comprising:
a sheath having a proximal end, a distal end and a lumen extending longitudinally therethrough;
an attachment member including an elongated member having a proximal end, a distal end and a lumen extending longitudinally therethrough, said attachment member disposed in said lumen of said sheath, said attachment member including at least one sleeve circumferentially disposed about said elongated member; and
a suture having opposing ends, one of said opposing ends attached to said anchor.

31. The anchor of claim 30, wherein said anchor further comprises a second sleeve, said second sleeve disposed about said elongated member in spaced relation to said at least one sleeve.

32. The anchor of claim 30, wherein said one of said opposing ends is attached to said attachment member.

33. A kit for anchoring a viscus to a body wall, comprising:
a needle;
a suture anchor device, said device comprising:
a first sheath having a proximal end, a distal end and a lumen extending longitudinally therethrough;
a reinforcing member having a proximal end, a distal end and a lumen extending longitudinally therethrough, said reinforcing member disposed in said lumen of said first sheath;
a visceral anchor comprising:
a second sheath having a proximal end, a distal end and a lumen extending longitudinally therethrough, said proximal end of said second sheath abutting said distal end of said first sheath;
a suture having a first secured region and a second secured region, said first secured region being attached to said anchor; and
an attachment member disposed within said lumen of said second sheath and configured to secure said suture.

34. The kit of claim 33, further including a wire guide.

35. A kit for anchoring a viscus to a body wall, comprising:
a needle;
a suture anchor device, said device comprising:
a first sheath having a proximal end, a distal end and a lumen extending longitudinally therethrough;
a reinforcing member having a proximal end, a distal end and a lumen extending longitudinally therethrough, said reinforcing member disposed in said lumen of said first sheath;
a second sheath having a proximal end, a distal end and a lumen extending longitudinally therethrough, said proximal end of said second sheath abutting said distal end of said first sheath;
an elongated member disposed in said lumen of said second sheath, said elongated member having a proximal end, a distal end, a lumen extending longitudinally therethrough; and
a suture having a first secured region and a second secured region, said first secured region being attached to said elongated member.

36. The kit of claim 35, further including a wire guide.

37. A method for anchoring a viscus to a body wall of a patient, said viscus having an interior viscus wall and a viscus lumen, said method comprising:
providing a tract from outside of the body through the skin and said interior viscus wall to said viscus lumen, the tract having a longitudinal axis extending from outside the body to said viscus lumen;
positioning a suture anchor device through said tract and in said viscus lumen, said device comprising:
a first sheath having a proximal end, a distal end and a lumen extending longitudinally therethrough;
a reinforcing member having a proximal end, a distal end and a lumen extending longitudinally therethrough, said reinforcing member disposed in said lumen of said first sheath; and
a visceral anchor including:
a second sheath having a proximal end, a distal end and a lumen extending longitudinally therethrough, said proximal end of said second sheath abutting said distal end of said first sheath;
a suture having a first secured region and a second secured region, the first secured region being attached to said anchor; and
an attachment member disposed within said lumen of said second sheath and configured to secure said suture;

deploying said anchor into said viscus lumen; and moving said proximal end of said suture to draw said anchor against the interior wall of said viscus so that said viscus is pulled against the body wall.

38. The method of claim 37, wherein said proximal end of said suture is attached to a suture needle.

39. The method of claim 37, said method further comprising anchoring said suture outside of the body to retain said viscus against the body wall.

40. The method of claim 37, wherein said anchoring comprises inserting said suture needle into the skin of said body.

41. The method of claim 37, wherein said device further comprises a suture securing means.

42. The method of claim 41, wherein said suture securing means comprises a cap mounted at said proximal end of said first sheath, said cap having a locking slot.

43. The method of claim 42, wherein said deploying said anchor comprises removing said suture from said locking slot of said cap.

44. The method of claim 37, wherein said deploying said anchor comprises moving said reinforcing member relative to said first sheath so that said anchor is deployed in said viscus lumen.

45. The method of claim 37, wherein said providing a tract from outside of the body through the skin and said interior viscus wall to said viscus lumen comprises making a puncture by inserting a needle through the skin and into said viscus lumen.

46. The method of claim 45, wherein said needle has a lumen.

47. The method of claim 46, further comprising inserting a wire guide through said lumen of said needle and into said viscus lumen and removing said needle.

48. A method for anchoring a viscus to a body wall of a patient, said viscus having an interior viscus wall and a viscus lumen, said method comprising:

puncturing the skin with a needle having a lumen to provide a tract from outside of the body through the skin and said interior viscus wall to said viscus lumen, the tract having a longitudinal axis extending from outside the body to said viscus lumen;

inserting a wire guide through the lumen of said needle and into said viscus lumen;

removing said needle;

positioning a suture anchor device through said tract and in said viscus lumen, said device comprising:

a first sheath having a proximal end, a distal end and a lumen extending longitudinally therethrough;

a reinforcing member having a proximal end, a distal end and a lumen extending longitudinally therethrough, said reinforcing member disposed in said lumen of said first sheath; and a visceral anchor comprising:

a second sheath having a proximal end, a distal end and a lumen extending longitudinally therethrough, said proximal end of said second sheath abutting said distal end of said first sheath;

a suture having a first secured region and a second secured region, the first secured region being attached to said anchor; and an attachment member disposed within said lumen of said second sheath and configured to secure said suture;

deploying said anchor into said viscus lumen; and moving said proximal end of said suture to draw said anchor against the interior wall of said viscus so that said viscus is pulled against the body wall.

49. A method for anchoring a viscus to a body wall of a patient, said viscus having an interior viscus wall and a viscus lumen, said method comprising:

providing a tract from outside of the body through the skin and said interior viscus wall to said viscus lumen, the tract having a longitudinal axis extending from outside the body to said viscus lumen;

positioning a suture anchor device through said tract and in said viscus lumen, said device comprising:

a first sheath having a proximal end, a distal end and a lumen extending longitudinally therethrough;

a reinforcing member having a proximal end, a distal end and a lumen extending longitudinally therethrough, said reinforcing member disposed in said lumen of said first sheath;

a second sheath having a proximal end, a distal end and a lumen extending longitudinally therethrough, said proximal end of said second sheath abutting said distal end of said first sheath;

an attachment member including an elongated member having a proximal end, a distal end and a lumen extending longitudinally therethrough, said attachment member disposed in said lumen of said second sheath, said attachment member including at least one sleeve circumferentially disposed about said elongated member; and a suture having a first secured region and a second secured region, said first secured region being attached to said device;

deploying said anchor into said viscus lumen; and moving said proximal end of said suture to draw said anchor against the interior wall of said viscus so that said viscus is pulled against the body wall.

50. The method of claim 49, wherein said first secured region is attached to said attachment member.

51. The method of claim 47, wherein said wire guide is a micro wire guide.

52. A surgical apparatus adapted to be inserted through a body wall to form an anchor relative to the body wall comprising:

a two piece dilator having a first piece and a releasable second piece, said first piece being an outer cannula having a near end and a far end, the outer cannula having an outer surface and an inner surface extending between the near end and the far end, the inner surface defining a first passageway extending generally along a first axis between the near end and far end, said releasable second piece having a first end and a second end, said second piece having an outward facing surface and an inward facing surface extending between the first end and the second end, the inward facing surface defining a second passageway extending generally along a second axis between the first end and second end;

a pull string having a first end and a second end, the second end of said pull string being attached to said second piece;

an elongated member having a proximal end and a distal end, said member having an outer surface and an inner surface extending between the proximal end and the distal end, the inner surface of said member defining a third passageway extending between the proximal end and distal end, said member adapted to fit within the first passageway of said first piece; and, said apparatus having a first mode wherein said member is generally disposed within the first passageway and the distal end of said member acts as a telescoping joint such that said first piece and said second piece are associated with one another and the first axis is substantially parallel to the second axis, the distal end of said member extending beyond the far end of said first piece and into the first end of the second passageway in the first mode, and said apparatus having a second mode wherein said second piece is released when the distal end of said member is substantially withdrawn from the second passageway.

53. The apparatus of claim 52, wherein the second end of said second piece is tapered.

54. The apparatus of claim 52, wherein the first axis is substantially coaxial with the second axis in the first mode.

* * * * *

UNITED STATES PATENT AND TRADEMARK OFFICE
CERTIFICATE OF CORRECTION

PATENT NO. : 6,110,183
DATED : August 29, 2000
INVENTOR(S) : Constantin Cope

It is certified that error appears in the above-identified patent and that said Letters Patent is hereby corrected as shown below:

Column 1,
Line 15, begin a new paragraph after "reinserted." and before "Various".

Column 2,
Line 21, change "guide preferably a wire guide" to -- wire guide, preferably a micro wire guide --.
Line 36, change "A wire preferably a micro guide" to -- A wire guide, preferably a micro wire guide, --.

Column 5,
Line 50, begin a new paragraph after "sheath 31." and before "In".

Column 7,
Line 15, delete "30".

Column 10,
Line 58, change "the" to -- The --.

Signed and Sealed this

Fourth Day of December, 2001

*Attest:*

*Attesting Officer*

NICHOLAS P. GODICI
*Acting Director of the United States Patent and Trademark Office*